(12) United States Patent
Tanaka et al.

(10) Patent No.: US 9,259,205 B2
(45) Date of Patent: Feb. 16, 2016

(54) ULTRASOUND IMAGE CAPTURE DEVICE, ULTRASOUND IMAGE CAPTURE METHOD, ULTRASOUND IMAGE CAPTURE PROGRAM

(75) Inventors: Tomohiko Tanaka, Hino (JP); Takashi Azuma, Fuchu (JP); Kunio Hashiba, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 270 days.

(21) Appl. No.: 13/990,063

(22) PCT Filed: Nov. 28, 2011

(86) PCT No.: PCT/JP2011/077323
§ 371 (c)(1),
(2), (4) Date: Jul. 16, 2013

(87) PCT Pub. No.: WO2012/073863
PCT Pub. Date: Jun. 7, 2012

(65) Prior Publication Data
US 2013/0289408 A1 Oct. 31, 2013

(30) Foreign Application Priority Data
Nov. 30, 2010 (JP) ................................. 2010-266486

(51) Int. Cl.
*A61B 8/00* (2006.01)
*A61B 8/06* (2006.01)
*A61B 8/08* (2006.01)

(52) U.S. Cl.
CPC ................. *A61B 8/06* (2013.01); *A61B 8/0891* (2013.01); *A61B 8/5246* (2013.01); *A61B 8/0883* (2013.01)

(58) Field of Classification Search
CPC ............. A61B 8/00; A61B 8/06; A61B 8/483
See application file for complete search history.

(56) References Cited

U.S. PATENT DOCUMENTS

| 5,241,473 | A | 8/1993 | Ishihara et al. | |
| 5,622,174 | A | 4/1997 | Yamazaki | |
| 7,758,507 | B2 * | 7/2010 | Yoshikawa et al. | 600/441 |
| 8,480,590 | B2 * | 7/2013 | Tamura | 600/457 |
| 8,870,813 | B2 * | 10/2014 | Ferren et al. | 604/66 |

(Continued)

FOREIGN PATENT DOCUMENTS

| CN | 101636113 | 1/2010 |
| CN | 101828929 | 9/2010 |

(Continued)

OTHER PUBLICATIONS

International Search Report, International Application No. PCT/JP2011/077323, Filed Nov. 28, 2011, Mailed Dec. 27, 2011, ISA/Japanese Patent Office.

(Continued)

*Primary Examiner* — Joel Lamprecht
(74) *Attorney, Agent, or Firm* — Brundidge & Stanger, P.C.

(57) ABSTRACT

Provided is a technology which quantitatively measures blood flow in the vicinity of circulatory organs. An ultrasound image capture device according to the present invention removes an image portion corresponding to an organ shape by taking the difference of a multi-frame ultrasound image, and thereafter computes a measured value of a blood flow velocity vector on the basis of a plurality of images at different timings (as per FIG. 3).

12 Claims, 10 Drawing Sheets

(56) References Cited

U.S. PATENT DOCUMENTS

| | | |
|---|---|---|
| 2005/0075568 A1 | 4/2005 | Moehring |
| 2005/0124885 A1 | 6/2005 | Abend et al. |
| 2006/0184032 A1 | 8/2006 | Shiki |
| 2008/0015440 A1 | 1/2008 | Shandas et al. |
| 2010/0069757 A1 | 3/2010 | Yoshikawa |

FOREIGN PATENT DOCUMENTS

| | | |
|---|---|---|
| EP | 0226044 A2 | 6/1987 |
| JP | 62-114539 | 5/1987 |
| JP | 05-31112 | 2/1993 |
| JP | 2010-503421 | 2/2010 |

OTHER PUBLICATIONS

Jun-ichi Suzuki, et al.; "Vector Analysis of the Hemodynamics of Atherogenesis in the Human Thoracic Aorta Using MR Velocity Mapping", 1998.

Chinese Foreign Office Action.

* cited by examiner

FIG. 7
(a)
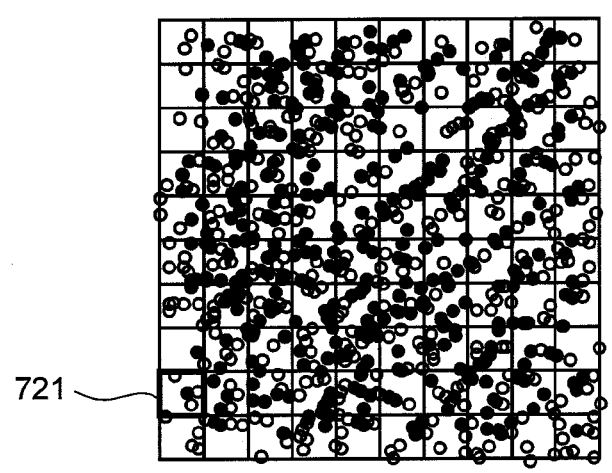
(b)
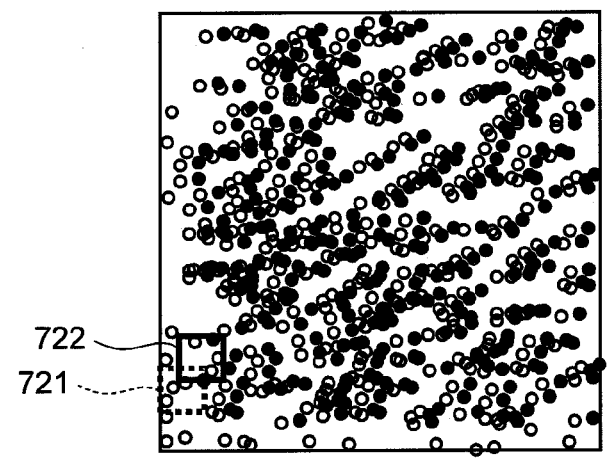
(c)
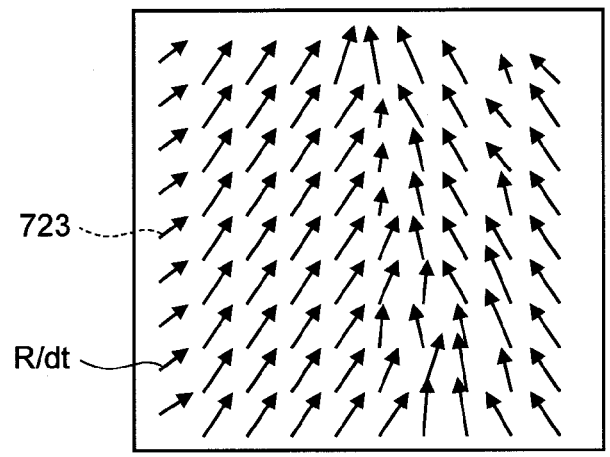

FIG. 9
(a)
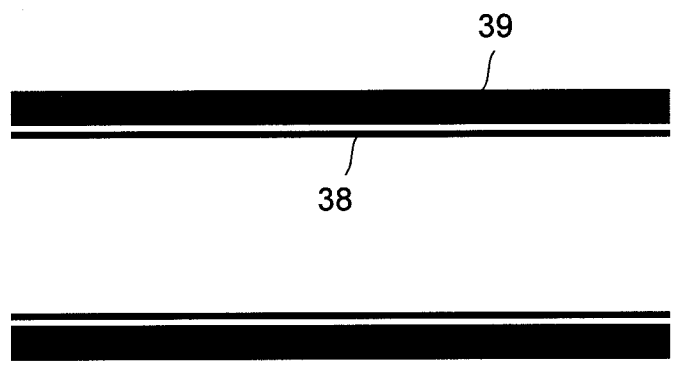
(b)
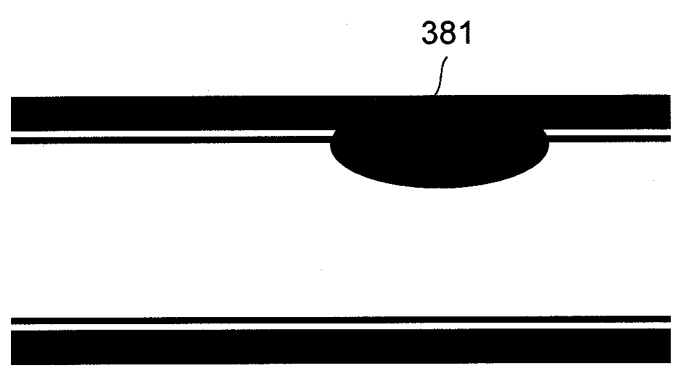
(c)
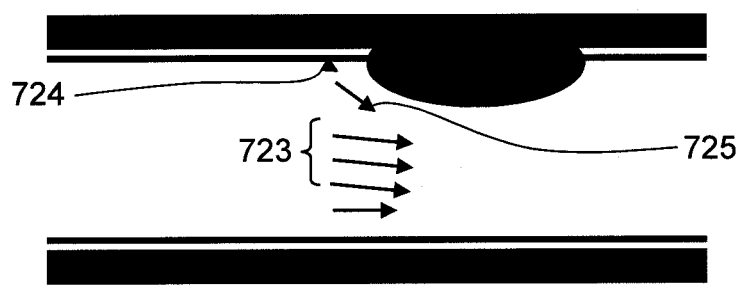

ULTRASOUND IMAGE CAPTURE DEVICE, ULTRASOUND IMAGE CAPTURE METHOD, ULTRASOUND IMAGE CAPTURE PROGRAM

TECHNICAL FIELD

The present invention relates to a technique for imaging ultrasound images.

BACKGROUND ART

In circulatory system that circulates bloods in body, efficiencies and forms of blood circulation have a close relation with circulatory diseases. For example, a circulatory system with low efficiency stresses the heart, which increases a risk of heart failure. The efficiency of blood circulation can be described by momentum or energy of blood.

Not only regarding heart but also in blood vessel disease such as arteriosclerosis, it has become apparent that a shear stress describing a kinetic exchange between a blood vessel and a blood flow when the blood flows is closely concerned with diseases (Non Patent Literature 1).

In order to examine circulation efficiency or blood flow dynamic state of a circulatory tissue, it is required to acquire the mechanistic mutual relation between the circulatory tissue and the blood flow. In order to achieve it, it is required to quantitatively calculate the circulatory tissue motion and the blood flow vector around the boundary between the circulatory tissue and the blood flow, and to digitize its effects to analyze them.

Patent Literature 1 listed below describes a method for calculating a blood flow vector by integrating a plurality of differential images.

CITATION LIST

Patent Literature

Patent Literature 1: JP Patent Publication (Kokai) No. H05-31112 A (1993)

Non Patent Literature

Non Patent Literature 1: Suzuki, J et al. Am. J. Roentgenology. 171:1285-1290 (1998)

SUMMARY OF INVENTION

Technical Problem

In the technique described in the Patent Literature 1, brightness values of pixels vary along the movement direction in a graded fashion, thus the motion vector can be visually recognized according to the change in brightness. However, the blood flow vector is analyzed by changes in brightness or color, thus the blood flow can only be sensed or identified qualitatively.

In order to examine circulation efficiency or blood flow dynamic state of a circulatory tissue, it is required to numerically analyze the mechanistic mutual relation between the circulatory tissue and the blood flow. Therefore, the method described in the Patent Literature 1 may not be able to acquire sufficient analytical results.

The present invention has been made to solve the problem stated above, and it is an objective of the present invention to provide a technique for quantitatively measuring blood flows around circulatory tissues.

Solution to Problem

The ultrasound imaging device according to the present invention removes image portions corresponding to tissue shapes by obtaining differences between a plurality of frames of ultrasound images, and calculates measured values of blood flow velocity vector based on a plurality of images at different times.

Advantageous Effects of Invention

With an ultrasound imaging device according to the present invention, even in a case where reflected signals obtained from blood flows around circulatory tissues are weak, it is possible to emphasize blood flows by removing image portions corresponding to tissue shapes. This enables more precise measurement of blood flows.

BRIEF DESCRIPTION OF DRAWINGS

FIG. 7 is a diagram showing a processing image in step S2032.

FIG. 9 is a side cross-sectional diagram of a subject 3 (artery).

DESCRIPTION OF EMBODIMENTS

Embodiment 1

Figure 1:
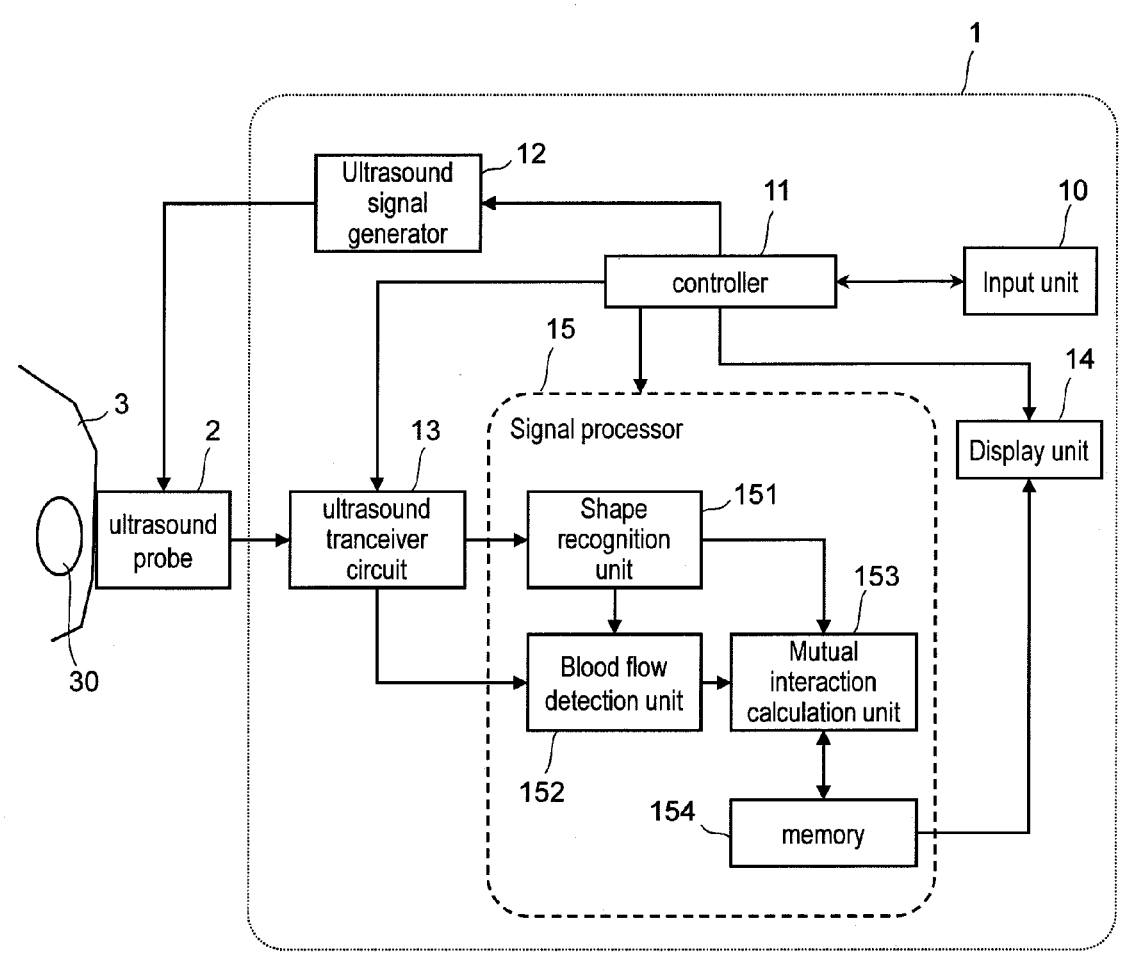
FIG. 1 is a functional block diagram of an ultrasound imaging device according to an embodiment 1 of the present invention.

FIG. 1 is a functional block diagram of an ultrasound imaging device according to an embodiment 1 of the present invention. The ultrasound imaging device 1 is a device that irradiates an ultrasound wave from an ultrasound probe 2 to a subject 3 (e.g. biological body), receives a reflected echo signal, and generates an ultrasound image of the subject. The ultrasound probe 2 irradiates an ultrasound wave to an irradiation region 30 of the subject 3 according to a signal generated by an ultrasound signal generator 12, and receives a reflected echo signal of the irradiation region 30.

The ultrasound imaging device 1 includes an input unit 10, a controller 11, the ultrasound signal generator 12, an ultrasound receiver circuit 13, a display unit 14, and a signal processor 15. "ultrasound transceiver" in the present invention corresponds to the controller 11, the ultrasound signal generator 12, and the ultrasound receiver circuit 13.

The input unit 10 is an operation device for operators who operate the ultrasound imaging device 1 to instruct operational conditions of the ultrasound imaging device 1 and the like to the controller 11. The input unit 10 can be configured using a keyboard, a pointing device, or the like. The input unit 10 can also be used when an operator inputs cardiac electrogram signals in a case using the cardiac electrogram.

The controller 11 controls, according to operational conditions of the ultrasound imaging device 1 configured by the input unit 10, the ultrasound signal generator 12, the ultrasound receiver circuit 13, the display unit 14, and the signal processor 15. The ultrasound receiver circuit 13 performs a signal processing such as amplification or phasing to the reflected echo signals received by the ultrasound probe 2. The ultrasound receiver circuit 13 includes a receiver circuit, means for detecting envelopes, and means for performing Log compression. The ultrasound receiver circuit 13 may include a scan converter. In this case, it is beneficial to decrease the amount of data to be processed. Alternatively, the scan converter may not be included in the ultrasound receiver circuit 13 and the signal processor 15 may process a lot of data to implement a measurement device with high precision. The scan converter may be used after calculation. The sampling frequency of an A/D converter is between 20 MHz and 50 MHz. The display unit 14 displays information generated by the signal processor 15. The signal processor 15 generates an ultrasound image from the reflected echo signal received by the ultrasound probe 2.

The signal processor 15 includes a shape recognition unit 151, a blood flow detection unit 152, a mutual interaction calculation unit 153, and a memory 154.

The shape recognition unit 151 creates, from the reflected echo signal outputted by the ultrasound receiver circuit 13, 2D tissue shape information of the subject 3 using planar imaging method or 3D tissue shape information (e.g. B mode image) of the subject 3 using stereoscopic imaging method. The raster interval of B mode is within from one-tenth to four times of the width of ultrasound point spread function. The shape recognition unit 151 also calculates, from the generated tissue shape information, tissue location information describing the tissue location of the subject 3.

The blood flow detection unit 152 calculates a blood flow velocity vector from the tissue shape information created by the shape recognition unit 151. The blood flow detection unit 152 applies, using the tissue location information created by the shape recognition unit 151, a fluid physical law around the boundary between the subject tissue and the blood flow to correct the blood flow velocity vector. Details will be described later.

The mutual interaction calculation unit 153 calculates, from the blood flow velocity vector calculated by the blood flow detection unit 152, physical amounts working between the subject tissue and the blood flow or clinical indicators. Details will be described later.

The memory 154 stores the reflected echo signal received by the ultrasound probe 2, and information created by the shape recognition unit 151, the blood flow detection unit 152, and the mutual interaction calculation unit 153.

The controller 11, the signal processor 15, and functional units that belong to them can be configured by using hardware such as circuit devices implementing these functions, or can be configured by processors such as microcomputers or CPUs (Central Processing Unit) and software defining the processor's behaviors.

Figure 2:
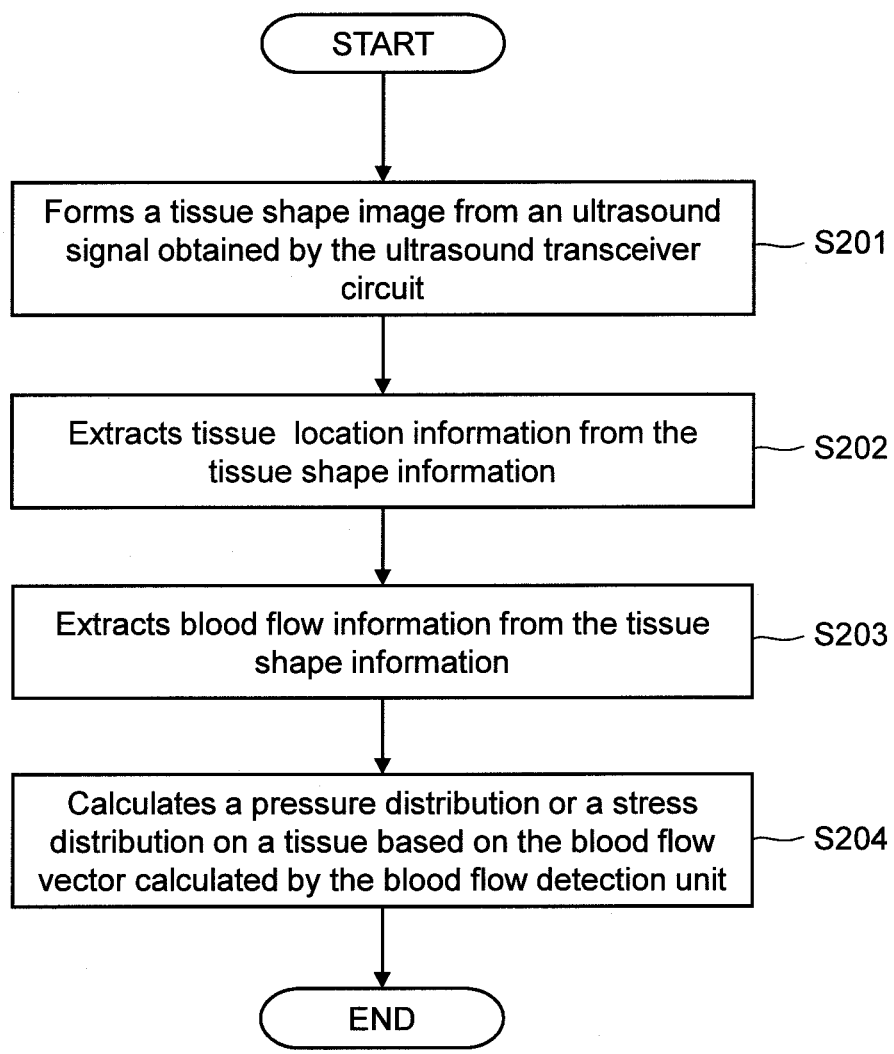
FIG. 2 is a diagram showing an operational flow of the ultrasound imaging device 1.

FIG. 2 is a diagram showing an operational flow of the ultrasound imaging device 1. In FIG. 2, the subject 3 is a heart and the irradiation region 30 is a portion including a left ventricle and a right ventricle. The irradiation region 30 is not limited to above and it may be portions such as blood vessels or other heart chambers.

(FIG. 2: step S201)

The shape recognition unit 151 creates, from the reflected echo outputted by the ultrasound receiver circuit 13, an ultrasound image (tissue shape image) such as B mode image showing the tissue shape of the subject 3. The shape recognition unit 151 obtains a plurality of the ultrasound images sequentially in chronological order.

(FIG. 2: Step S202)

The shape recognition unit 151 obtains, from the ultrasound images created in step S201, tissue location information of the subject 3. Specifically, the shape recognition unit 151 identifies locations of biological tissues such as heart tissues or blood vessels to create location information of those tissues. The tissue location may be identified by detecting inner walls of tissues using image processing. Alternatively, an operator of the ultrasound imaging device 1 may specify the inner walls of tissues through the input unit 10 to identify the tissue location.

(FIG. 2: Step S203)

The blood flow detection unit 152 emphasizes blood flow portions in the ultrasound images created by the shape recognition unit 151, and measures the blood flow velocity around the boundary between the biological tissue and the blood flow of the subject 3. The blood flow detection unit 152 corrects the obtained blood flow velocity by applying a physical consistency under fluid mechanics to the obtained blood flow velocity.

(FIG. 2: Step S203: Supplementation)

The physical consistency under fluid mechanics in this step is a restriction such as, for example: blood flow reflects on inner walls of blood vessels; the blood flow velocity at the portions contacting with inner walls of blood vessels is 0; and the like. Specific examples will be described later.

(FIG. 2: Step S204)

The mutual interaction calculation unit 153 calculates, from the tissue location information obtained by the shape recognition unit 151 and the blood flow velocity obtained by the blood flow detection unit 152, a physical mutual interaction between biological tissues and blood flows of the subject 3. For example, blood pressure distribution in the blood vessels, shear stresses generated by the blood flow on inner walls of the blood vessels of the subject 3, workloads of the blood flow, volumes of the blood flow, and the like can be considered.

(FIG. 2: Step S204: Supplementation No. 1)

The mutual interaction calculation unit 153 may calculate, based on the above-mentioned physical interactions, other clinically useful indicators. For example, spatial distributions or temporal distributions of the above-described physical interactions can be calculated. In addition, their maximum values, minimum values, average values, integral values, or their proportions can also be calculated.

(FIG. 2: Step S204: Supplementation No. 2)

Clinically useful indicators in this step are indicators such as, for example, maximum blood pressure or minimum blood pressure. These indicators can be calculated from blood flow velocities and are useful indicators of circulatory diseases. Thus these indicators are calculated in this step. In addition to above, it has become apparent that shear stresses on inner walls of blood vessels generated by blood flows are one of contributory factors of arterial aneurysm and the like. Therefore, it is beneficial to calculate these physical factors as clinical indicators.

(FIG. 2: Step S204: Supplementation No. 3)

The display unit 14 displays physical interaction values, clinical indicator values, and the like calculated by the mutual interaction calculation unit 153. For example, the display unit 14 may display these values in the form of displaying temporal variations of blood pressure distributions with colors, displaying the maximum pressure/minimum pressure at each time, and the like.

Figure 3:
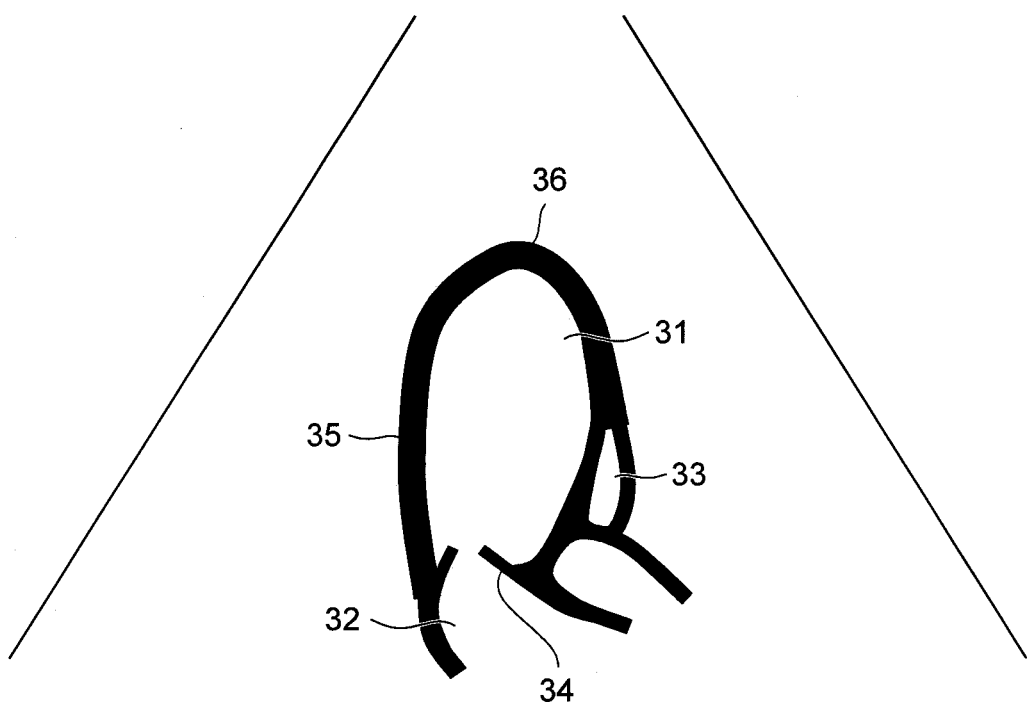
FIG. 3 is a diagram showing an example of a tissue shape image obtained in step S201.

FIG. 3 is a diagram showing an example of a tissue shape image obtained in step S201. A left ventricle 31, a left atrial 32, a right ventricle 33, a mitral valve 34, a left ventricular posterior wall 35, and a ventricular apex 36 of the subject 3 (heart) imaged by a 2D B mode are shown as examples. FIG. 3 shows 2D images as examples. However, 3D images are allowed. Ultrasound frequencies of B mode images are within 1 MHz to 20 MHz in which images can be obtained. In the embodiment 1, the central frequency is 5 MHz. The frame rate when imaging tissues varying along with heart beats is 20 Hz or more, because it is necessary to employ the frame rate within the scope in which the heart movement can be captured.

In step S202, the shape recognition unit 151 detects, by image processing, location information of tissue shape images obtained in step S201. Specifically, since tissue images have high brightness values in ultrasound images, the locations that include high brightness values can be regarded as locations that include heart tissues. This process may identify two-dimensional or three-dimensional heart tissue locations. In addition to above, the operator of the ultrasound imaging device 1 may designate, via the input unit 10, locations of tissue inner walls that are boundaries between blood flows and heart tissues to specify the tissue locations. Furthermore, in order to detect edges of tissue inner walls, methods using energy functions of brightness values such as generally referred to as SNAKES can be used.

Overall operations of the ultrasound imaging device 1 have been described thus far. Hereinafter, details of each step in FIG. 2 will be described with reference to Figures.

Figure 4:
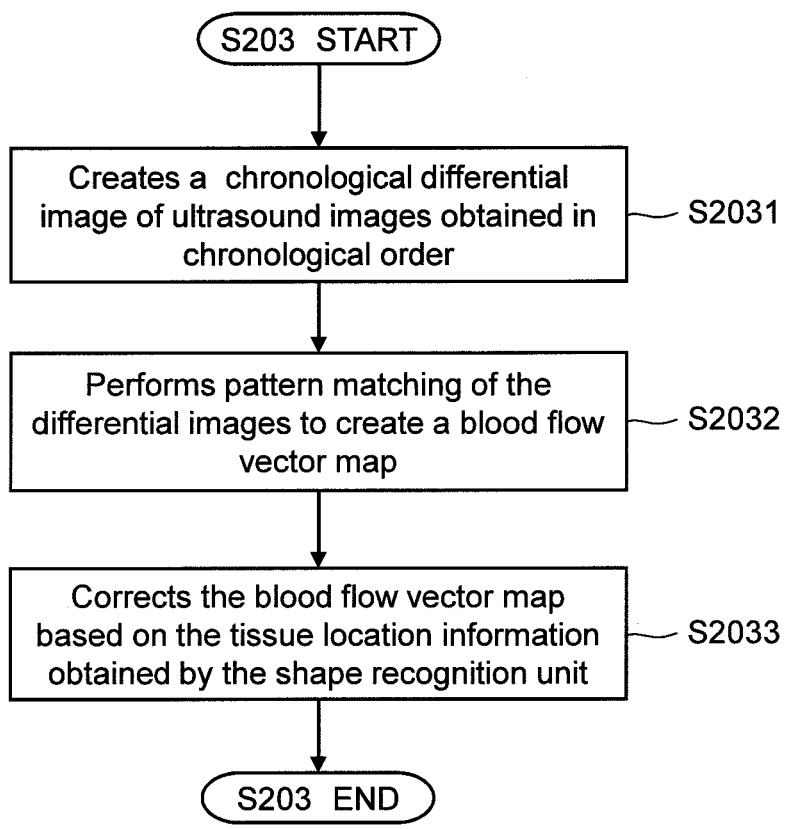
FIG. 4 is a diagram showing a detailed flow of step S203.

FIG. 4 is a diagram showing a detailed flow of step S203. An example of an ultrasound image on which this process flow is based will be shown in FIG. 5 described later. Processing images in each step will be shown in FIGS. 5 to 8 described later. Hereinafter, each step of FIG. 4 will be described.

(FIG. 4: Step S2031)

The blood flow detection unit 152 calculates a difference between frames of the ultrasound images obtained by the shape recognition unit 151 in chronological order to create differential images. Generally, reflected echo signals from scatterers injected in blood for measuring blood flow are smaller than reflected echo signals from biological tissues. Thus it is difficult to identify blood flows from ultrasound images. However, according to this step, reflected echo signal components from biological tissues are canceled on images to emphasize reflected echo signal components from scatterers in blood, thereby allowing measuring blood flows to be easier. A processing image in this step will be shown in FIG. 6 described later.

(FIG. 4: Step S2032)

The blood flow detection unit 152 performs pattern matching between the differential images created in step S2031 to calculate blood flow velocity vectors. The differential images mainly include reflected echo signal components from scatterers in blood. Therefore, it is possible to calculate blood flow motion vectors by performing pattern matching between the differential images. A processing image in this step will be shown in FIG. 7 described later.

(FIG. 4: Step S2033)

The blood flow detection unit 152 applies fluid physical laws around boundaries between the subject tissue and the blood flow using the tissue location information created by the shape recognition unit 151 and the blood flow vector calculated in step S2032, thereby correcting the blood flow velocity vector. A processing image in this step will be shown in FIG. 8 described later.

Figure 5:
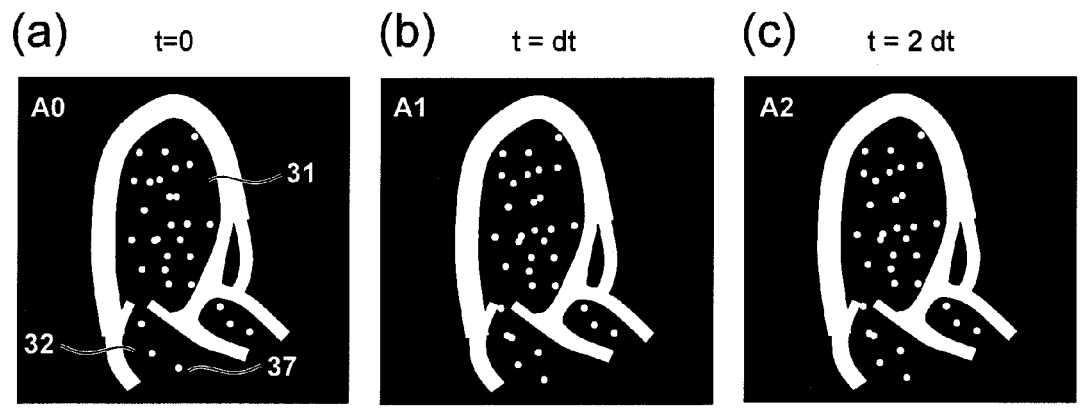
FIG. 5 is a diagram showing an example of an ultrasound image acquired by a shape recognition unit 151 in chronological order in step S201.

FIG. 5 is a diagram showing an example of ultrasound images obtained by the shape recognition unit 151 in chronological order in step S201. dt is the time interval for imaging. FIG. 5(a) shows an ultrasound image A0 at an arbitrary reference time t=0. FIG. 5(b) shows ultrasound images A1, A2 at t=dt and t=2dt, respectively. In the ultrasound images shown in FIG. 5, as an example of the subject 3, a left ventricle 31, a left atrial 32, and a scatterer 37 mixed in the blood are imaged. The scatterer may be a blood cell or an ultrasound contrast agent for amplifying signal strength.

Figure 6:
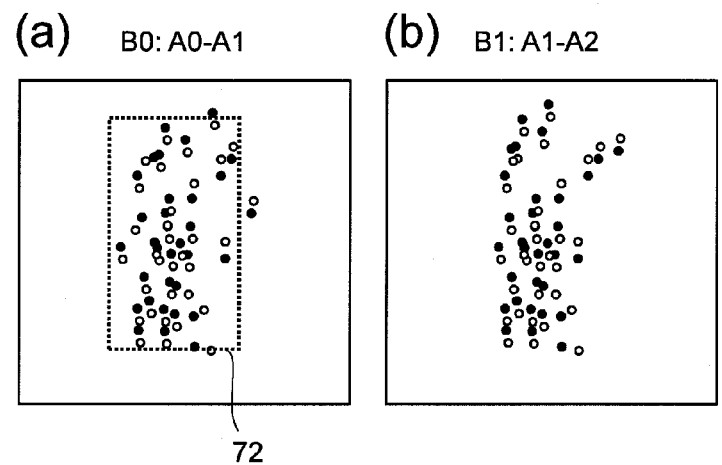
FIG. 6 is a diagram showing a processing image in step S2031.

FIG. 6 is a diagram showing a processing image in step S2031. FIG. 6(a) shows a differential image B0 between the ultrasound images A0 and A1 shown in FIG. 5. FIG. 6(b) shows a differential image B1 between the ultrasound images A1 and A2 shown in FIG. 5. The region of interest (ROI) 72 in FIG. 6 will be described later in FIG. 7.

In the differential image B0, if the blood flow velocity is sufficiently larger than the moving velocity of the biological tissue, the tissue components are removed and only the blood components remain in the differential image. This results in that the brightness value of backgrounds (biological tissue portions) on the differential image becomes almost 0. The scatterer in blood imaged in A0 becomes positive brightness value and the scatterer in blood imaged in A1 becomes negative brightness value to be shown in the differential image B0. In FIG. 6, positive brightness values are shown with white circles and negative brightness values are shown with block circles. When detecting velocity, an optical flow using differential values of brightness values can be used. Other than pattern matching, the center location of scatterers in blood can be identified from brightness values of the scatterer in blood and the center location of scatterers in blood for the next image can also be identified similarly, thereby calculating the displacement from the difference between those center locations. The velocity can be calculated by dividing the displacement by imaging intervals of the image. Other than the center locations of the image, feature points of the image can be extracted to detect the displacement of the feature points, then the displacements can be converted into velocity. The feature points are such as edges, polygonal lines, or circles.

The blood flow detection unit 152 calculates blood flow velocity vectors by obtaining displacements of scatterers in blood using pattern matching in step S2032. Other than calculating blood flow velocity vectors by pattern matching, above-described methods can be employed. Any method can be used as long as the method include a function for calculating blood flow velocity vectors based on a plurality of images at different times after the images showing tissue shapes of the subject are removed. The present invention is not limited to employing pattern matching.

If biological tissues are included in the image, the reflected echo signals from blood flows around the boundary between the biological tissue and the blood flow will be blurred by the reflected echo signals from the biological tissue. Therefore, in step S2031, the signal strength is decreased by canceling the reflected echo signal components from the biological tissue. Specifically, the differential image can be obtained by subtracting brightness values of each pixel between frames.

FIG. 7 is a diagram showing a processing image in step S2032. FIG. 7(a) shows an ultrasound image in the ROI 72 at t=0. FIG. 7(b) shows an ultrasound image in the ROI 72 at t=dt. The ROI 72 corresponds to the image region in which the blood flow velocity vector will be calculated. In order to obtain spatial velocity information, behaviors of each scatterer in blood can be tracked. However, in FIG. 7, the ROI at a certain time is divided into grids and image patterns of scatterers in blood are tracked.

The blood flow detection unit 152 searches, by pattern matching, a grid 722 in FIG. 7(b) that corresponds to the image pattern of a grid 721 in FIG. 7(a). Namely, the blood flow detection unit 152 identifies the location in FIG. 7(b) to which the scatterer in blood in the grid 721 of FIG. 7(a) has moved. This enables calculating the displacement of the grid 721 between FIG. 7(a)(b).

Assuming that the displacement of the grid 721 is R, the velocity of the grid 721 can be calculated by R/dt. The blood flow detection unit 152 can calculate a spatial velocity vector 723 as shown in FIG. 7(c) by obtaining velocities for all grids similarly.

The blood flow detection unit 152 may calculate spatial velocity vectors by performing pattern patching for each of scatterer particles in blood instead of performing pattern matching for each of grids as described above.

As another method for calculating spatial distributions of velocity vectors, a method using Doppler effect of ultrasound reflectors in blood such as blood cells can be employed. In addition, a method for calculating velocity vectors from velocity fields obtained by Doppler effect using current functions can be employed. However, the velocity information calculated by Doppler effect is a component of velocity vectors projected in the ultrasound projection direction only. Therefore, when using Doppler effect, angle correction is necessary and the component of the velocity vector in the ultrasound projection direction may cause errors. In addition, since stream functions assume 2D flow fields, spatial distributions of velocity vectors can be calculated using Doppler effect only in limited situations.

According to above-described discussions, the method for tracking scatterers in blood to three-dimensionally calculate flow fields may be optimum. A size appropriate for tracking tracers is selected as the size of grids. Specifically, the size is between 3 to 130 pixels.

Figure 8:
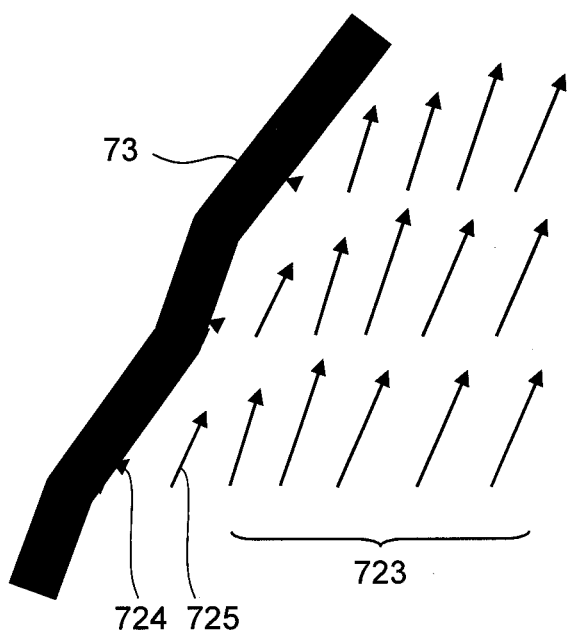
FIG. 8 is a diagram showing a processing image in step S2033.

FIG. 8 is a diagram showing a processing image in step S2033. The physical interaction between biological tissues and blood flows occur at the boundary between them. Therefore, the blood flow velocity around the boundary between the biological tissue and the blood flow is very important information. FIG. 8 will describe how to calculate it.

The blood flow detection unit 152 identifies the boundary between the biological tissue and the blood flow according to the tissue location information 73 calculated by the shape recognition unit 151. The blood flow detection unit 152 then applies a non-slipping boundary condition at the boundary surface, namely a physical law that the blood flow velocity is 0 at boundary, and assumes that a blood flow velocity vector 724 at the boundary is a zero vector.

[Equation 1]

$$\vec{V} = \vec{0}$$ (Formula 1)

When measuring vector mappings, the blood flow detection unit 152 may utilize the continuity of blood flow velocity distributions to calculate blood flow velocity vectors by interpolation. For example, the blood flow velocity is measured and is provided to the signal processor 15 via the input unit 10 or the like. Generally, if blood flow is actually measured, a blood flow velocity around center of blood vessels is obtained, not around inner walls of blood vessels. The blood flow detection unit 152 performs interpolation such as linear interpolation or spline interpolation for regions between the zero vector at the boundary and the measured value, thereby calculating velocity vectors at the intermediate regions. In FIG. 8, a zero velocity vector 724, a measured velocity vector 723, and an interpolated velocity vector 725 are described together.

Embodiment 1

Summary

As described thus far, the ultrasound imaging device 1 according to the embodiment 1 cancels biological tissue images of the subject 3 by calculating differential images between frames of ultrasound images. According to the configuration, even if the reflected echo signals from blood flows around the boundary between the biological tissues and the blood flows are smaller than the reflected echo signals from the biological tissues, it is possible to emphasize blood flow images to identify the blood flows more precisely.

In addition, the ultrasound imaging device 1 according to the embodiment 1 performs pattern matching for the images in which the biological tissue images are canceled, thereby calculating blood flow velocity vectors. According to the configuration, blood flow velocities can be quantitatively digitized using the images in which the blood flows are emphasized.

In addition, the ultrasound imaging device 1 according to the embodiment 1 identifies the boundary between the biological tissue of the subject 3 and the blood flow based on the tissue shapes recognized by the shape recognition unit 151. In addition, the ultrasound imaging device 1 applies a mechanics law that the blood flow velocity at the boundary becomes zero, and calculates or interpolates the blood flow velocity in other regions. According to the configuration, it is possible to improve calculation accuracy for blood flow velocity vectors.

Embodiment 2

In an embodiment 2 of the present invention, an operational example of the ultrasound imaging device 1 in which the subject 3 is an artery will be described. The configuration of the ultrasound imaging device 1 is the same as that of the embodiment 1. Thus differences will be mainly described below.

FIG. 9 is a side cross-sectional diagram of the subject 3 (artery). As shown in FIG. 9(a), the artery includes an arterial wall 39 and a blood vessel endothelium 38. In addition, as shown in FIG. 9(b), the artery may include an arterial aneurysm 381 in some cases. Hereinafter, differences from the embodiment 1 will be described for step S2033 described in FIG. 4.

(FIG. 4: Step S2033: Additional Features)

If the artery can be approximated as a cylinder, the blood flow detection unit 152 can calculate blood flow velocity vectors using flow analyze methods in cylinder. For example, the blood flow detection unit 152 performs analytical methods using Hagen-Poiseuille flow or Womersley's vibration analytical solution, thereby calculating blood flow velocity vectors in the artery.

(FIG. 4: Step S2033: Supplementation No. 1)

Even if the arterial aneurysm 381 exists, the shape of artery can be approximated by 2D planes as long as the artery can be approximated as a plane-symmetrical cylinder. In addition, a Doppler velocity may be measured in one direction, and a two-directional vector distribution may be obtained by using a stream function to the zero vector, thereby calculating blood flow velocity components in directions in which measured values are not obtained. Specific methods will be described below.

The blood flow velocity obtained by Doppler measurement is a component in a direction parallel to the ultrasound beam. Now it is assumed that the direction is x, a velocity component in the x direction is u, a direction perpendicular to x in the plane of ultrasound image is y, and a velocity component in the y direction is v. In a case where the planarity of flow field is maintained or in a case where changes in velocity of fluids intersecting the ultrasound images are small, the law of conservation of mass can be expressed as (Formula 2) shown below.

[Equation 2]

$$0 = \frac{\partial V_1}{\partial x_1} + \frac{\partial V_2}{\partial x_2} \quad \text{(Formula 2)}$$

By defining a stream function $\Phi$ as (Formula 3) and (Formula 4) shown below, (Formula 2) will be automatically satisfied.

[Equation 3]

$$\partial \Phi / \partial y = u \quad \text{(Formula 3)}$$

[Equation 4]

$$-\partial \Phi / \partial x = v \quad \text{(Formula 4)}$$

By differentiating (Formula 2) in the x direction and integrating in the y direction, a relational expression of (Formula 5) shown below will be derived.

[Equation 5]

$$\int \frac{\partial u}{\partial x} dy = \int \frac{\partial^2 \Phi}{\partial y \partial x} dy = \frac{\partial \Phi}{\partial x} = -v \quad \text{(Formula 5)}$$

By performing definite integration, a velocity $v_{c2}$ in the y direction at an arbitrary location C2 is described as (Formula 6) shown below.

[Equation 6]

$$v_{C2} = \int_{C1}^{C2} \frac{\partial u}{\partial x} dy + v_{C1} \quad \text{(Formula 6)}$$

Details of (Formula 6) will be described. In Doppler measurement, velocity components can be obtained only in one direction. When calculating the velocity $v_{c2}$ in the y direction at an arbitrary location C2, a velocity $v_{c1}$ in the y direction at a location having the same y-coordinate and an arbitrary x-coordinate must be known. By appropriately selecting a wall surface C0 at a location C1, (Formula 7) shown below will be obtained with a zero value of $v_{c0}$. In addition, by clarifying the location of wall surface, it is possible to integrate from C0 to C2, thereby calculating the velocity $v_{c2}$ in the y direction.

[Equation 7]

$$v_{C2} = \int_{C0}^{C2} \frac{\partial u}{\partial x} dy \quad \text{(Formula 7)}$$

Orthogonal coordinate system is described as an example thus far. However, a stream function of axial reference system can be employed.

(FIG. 4: Step S2033: Supplementation No. 2)

The suffixes 1 and 2 in (Formula 2) indicate coordinate axes perpendicular to each other in the ultrasound images. By using (Formula 1) and (Formula 2) to the blood flow velocity vectors measured by ultrasounds, it is possible to interpolate velocity distributions around the boundary between the artery tissues and the blood flows.

(FIG. 4: Step S2033: Supplementation No. 3)

FIG. 9(c) shows a pressure distribution diagram in the artery. The blood flow velocity vector on the artery inner wall 38 is the zero velocity vector 724. The blood flow velocities at the center of the artery can be obtained by actual measurement (measured velocity vector 723). The blood flow velocity vector 725 in the region between the measured velocity vector 723 and the zero velocity vector 724 can be calculated by interpolation as the embodiment 1 does.

Embodiment 2

Summary

As described thus far, the ultrasound imaging device 1 according to the embodiment 2 approximates the blood vessel as a cylinder, and estimates the blood flow velocity vectors in the blood vessel using fluid analytical methods in cylinder. In addition, if measured values of the blood flow velocity can be obtained, the blood flow velocity vector in the region between the measured velocity vector 723 and the zero velocity vector 724 is obtained by interpolation. According to the configuration, it is possible to precisely estimate the blood flow velocity vectors in the blood vessel.

In addition, the ultrasound imaging device 1 according to the embodiment 2 assumes that the blood vessel has a plane-symmetrical structure with a plane intersecting the center axis of the blood vessel as the symmetric plane, and approximates the blood vessel by a 2D plane. According to the configuration, the law of conservation of mass for fluids can be simplified, thereby estimating the blood flow velocity vectors in the blood vessel with small processing loads.

Embodiment 3

In an embodiment 3 of the present invention, a specific example of step S204 in FIG. 2 will be described. The configuration of the ultrasound imaging device 1 is the same as that of the embodiments 1 and 2.

The mutual interaction calculation unit 153 calculates physical interactions between the biological tissues and the blood flows according to the tissue location information of the subject 3 obtained by the shape recognition unit 151 and the blood flow velocity vectors obtained by the blood flow detection unit 152. The mutual interaction mentioned here can be calculated from a mutual interaction of stress, momentum exchange, energy exchange, and the like.

Mutual interaction of stress can be generally categorized into a stress in a direction parallel to the normal of the tissue boundary and a shear stress in a direction perpendicular to the normal.

Pressure distributions can be calculated by motion equation of fluids. Navier-Stokes equation describing a law of conservation of momentum for fluids as shown in (Formula 8) or Euler equation simplifying (Formula 8) as shown in (Formula 9) can be used as the motion equation.

[Equation 8]

$$\nabla P = -\rho\left(\frac{\partial V_i}{\partial t} + V_j \frac{\partial V_i}{\partial t}\right) + \mu \frac{\partial^2 V_i}{\partial x_j \partial x_j} \quad \text{(Formula 8)}$$

$$\nabla P = -\rho\left(\frac{\partial V_i}{\partial t} + V_j \frac{\partial V_i}{\partial t}\right) \quad \text{(Formula 9)}$$

$V_i$: i direction component of blood velocity vector V at an arbitrary location X in cardiac cavity $\nabla P$: pressure gradient at location X $\rho$: constant indicating blood density, $1000 \text{ Kg/m}^2 \leq \rho \leq 1100 \text{ Kg/m}^2$ $\mu$: constant indicating blood viscosity, $3500 \text{ Kg/m/s} \leq \mu \leq 5500 \text{ Kg/m/s}$ Hereinafter, a method for calculating pressure distributions using a pressure gradient will be described. When calculating a pressure gradient at a location X in which blood is flowing, the mutual interaction calculation unit 153 designates an arbitrary route L connecting a reference point $X_0$ and a location $X_1$, and calculates pressure gradients at discrete locations $L_1$, $L_2$, $L_3$, ..., $L_n$ in the route L using an arbitrary integer N. The mutual interaction calculation unit 153 then sums up products of pressure gradients at locations $L_1$, $L_2$, $L_3$, ..., $L_n$ at which the pressure gradients are calculated and distances between the discrete location. The sum is used as a pressure difference between the reference point $X_0$ and the location $X_1$. Pressure gradients in regions where flow rates are small may be 0 or may be a constant between −1 mmHg/cm and 1 mmHg/cm.

Figure 10:
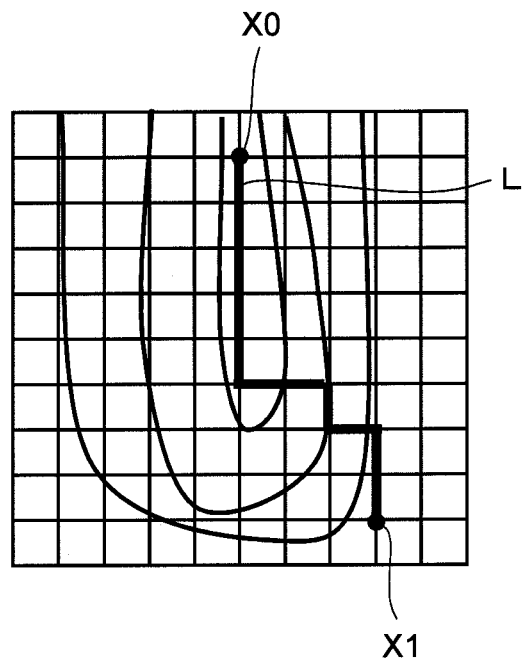
FIG. 10 is a diagram exemplifying a screen image when a display unit 14 displays a contour line of a pressure distribution.

FIG. 10 is a diagram exemplifying a screen image when the display unit 14 displays contour lines of pressure distribution. The mutual interaction calculation unit 153 can obtain contour lines of pressure difference distributions by performing the above-described processes for all grids. In addition, contour lines of pressure distribution as shown in FIG. 10 can be obtained by inputting through the input unit 10 estimated values of pressure at the reference point $X_0$.

The estimated value of pressure at the reference point $X_0$ may be estimated by using generalized transfer function method or may be estimated from blood pressure values of upper arms.

In addition, the mutual interaction calculation unit 153 may calculate the pressure distribution as chronological data. The mutual interaction calculation unit 153 may also calculate spatial distributions or temporal distributions and their maximum values, minimum values, integral values, and the like. The mutual interaction calculation unit 153 may calculate relative values of them to use the relative values as clinical indicators. The display unit 14 displays the indicators.

In addition, if valve stenosis occurs, pressure difference between upstream and downstream of the valve becomes larger, which imposes a burden on the heart. Therefore, the pressure difference itself is a useful clinical indicator. The display unit 14 may display spatial distributions or temporal distributions of the pressure difference.

Figure 11:
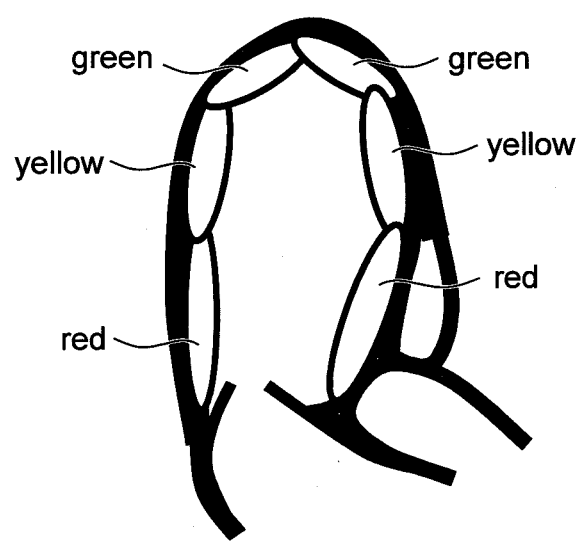
FIG. 11 is a diagram exemplifying a screen image when the display unit 14 displays a shear stress.

FIG. 11 is a diagram exemplifying a screen image when the display unit 14 displays shear stresses. As shown in FIG. 11, the color of edge portion may be changed depending on the magnitude of shear stress. As chronological data of the shear stress, temporally varied shear stresses may be calculated. In addition, maximum values, minimum values, or integral values of spatial distributions or temporal distributions may be calculated. Furthermore, relative values of them may be calculated as clinical indicators. The display unit 14 may display the indicators.

Further, since energy corresponds to a product of stress of blood flow and displacement of tissue, energy (i.e., a power provided by blood to tissue) can be calculated by calculating a displacement of tissues using tissue Doppler method or tissue tracking.

Specifically, in a case of diastolic failure, it is difficult to distinguish whether the cardiac dilatation is caused by a spontaneous relaxation or the heart is dilated due to bloods pressuring the cardiac muscle. It is possible to provide a useful indicator in diagnosing diastolic failure by inspecting mutual interactions between cardiac muscle and blood flow as the present invention does. In addition, the present invention can be applied to ischemic diagnosis by inspecting local mutual interactions between cardiac muscle and blood flow.

Figure 12:
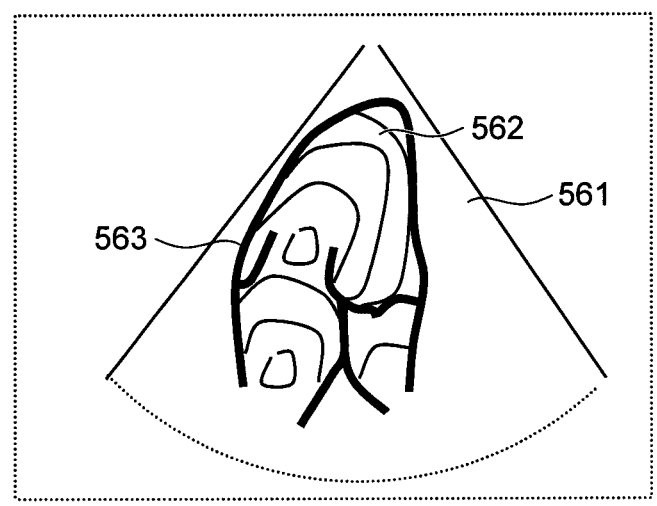
FIG. 12 is a diagram exemplifying a screen image when one or more of a pressure distribution, a shear stress distribution S of blood flow, and a vorticity distribution W is displayed.

FIG. 12 is a diagram exemplifying a screen image when the display unit 14 displays one or more of a pressure distribution, a shear stress distribution S of blood flow, and a vorticity distribution W at one or more spatial locations or at a certain time. The mutual interaction calculation unit 153 can calculate the shear stress distribution S of blood flow and the vorticity distribution W according to equations (Formula 10) and (Formula 11) below. The display unit 14 displays the calculation results.

[Equation 9]

$$S = \frac{\left(\frac{\partial V_i}{\partial x_j} + \frac{\partial V_j}{\partial x_i}\right)}{2} \quad \text{(Formula 10)}$$

$$W = \frac{\partial V_j}{\partial x_i} - \frac{\partial V_i}{\partial x_j} \quad \text{(Formula 11)}$$

The display unit 14 may display temporal variations of FIG. 12 in a movie format. The display unit 14 may also display it along with the images and tissue images created by the shape recognition unit 151 superimposed with each other. In addition, the display unit 14 may simultaneously display quantitative numerical values of stress or energy calculated by the mutual interaction calculation unit 153, or may display proportions of those values.

The display unit 14 may display, in addition to above, the process in which the signal processor 15 calculates the blood flow velocity vectors. For example, the calculation process performed in each step of flowcharts shown in FIG. 2 or 4, above-described formulas, images during calculations in FIGS. 5 to 9, and the like may be displayed.

The present invention has been described specifically according to the embodiments thus far. However, the present invention is not limited to the aforementioned embodiments and can be modified as long as not departing from the spirit of the invention.

REFERENCE SIGNS LIST

1: ultrasound imaging device, 10: input unit, 11: controller, 12: ultrasound signal generator, 13: ultrasound receiver circuit, 14: display unit, 15: signal processor, 151: shape recognition unit, 152: blood flow detection unit, 153: mutual interaction calculation unit, 154: memory, 2: ultrasound probe, 3: subject, 30: irradiation region, 31: left ventricle, 32: left atrial, 33: right ventricle, 34: mitral valve, 35: left ventricular posterior wall, 36: ventricular apex, 38: blood vessel endothelium, 39: arterial wall, 72: ROI, 721 to 722: grid, 723: measured velocity vector, 724: zero velocity vector, 725: interpolation velocity vector, 73: tissue location information.

The invention claimed is:

1. An ultrasound imaging device that images an ultrasound image, comprising:
   an ultrasound transceiver configured to irradiates an ultrasound wave to a subject and receives a reflected signal;
   a blood flow detection unit configured to detects a blood flow velocity in the subject using the reflected signal; and
   a shape recognition unit configured to recognize a tissue shape of the subject using the reflected signal;
   wherein the blood flow detection unit is configured to:
      remove an image portion indicating a tissue shape of the subject based on a plurality of ultrasound images of the subject created by using the reflected signal at different times,
      calculate a blood flow velocity vector in the subject based on a plurality of images at different times in which the image portion indicating the tissue shape of the subject is removed,
      identify a boundary surface between a tissue of the subject and a blood flow based on a recognition result of the shape recognition unit, and
      calculate or correct the blood flow velocity by applying a consistent condition under a fluid mechanics on the boundary surface.

2. The ultrasound imaging device of claim 1, wherein the blood flow detection unit is further configured to calculate the blood flow velocity vector in the subject by performing a pattern matching between the plurality of ultrasound images.

3. The ultrasound imaging device of claim 1, wherein the blood flow detection unit is further configured to:
   assume that the blood flow velocity at the boundary surface between the tissue of the subject and the blood flow is 0, and
   calculate or correct the blood flow velocity at other portions.

4. The ultrasound imaging device of claim 1, wherein the blood flow detection unit is further configured to:
   obtain a measured value of the blood flow velocity, and
   interpolate a blood flow velocity at a portion in which the measured value is not obtained by approximating a blood vessel shape of the subject as a cylinder to calculate the blood flow velocity in the cylinder.

5. The ultrasound imaging device according to claim 4, wherein the blood flow detection unit is further configured to:
   obtain a measured value of the blood flow velocity, and
   interpolate a blood flow velocity at a portion in which the measured value is not obtained by approximating a shape of the cylinder on a two-dimensional plane under an assumption that the blood vessel of the subject has a plane-symmetrical structure to calculate the blood flow velocity using a law of conservation of mass on the two-dimensional plane.

6. The ultrasound imaging device of claim 4, wherein the blood flow detection unit is further configured to calculate, using a stream function, a blood flow velocity component in a direction in which the measured value is not obtained.

7. The ultrasound imaging device of claim 1, further comprising a mutual interaction calculation unit configured to:
   calculate a physical quantity of a blood flow of the subject that provides an effect on a tissue of the subject, and
   calculate, as the physical quantity, one or more of a pressure distribution caused by the blood flow in the subject, a shear stress caused by the blood flow on a blood vessel inner wall of the subject, a power of the blood flow, and a flow volume of the blood flow.

8. The ultrasound imaging device of claim 1, further comprising:
   a display unit configured to displays at least one of a spatial distribution or a temporal distribution for one or more of a pressure distribution caused by a blood flow in the subject, a shear stress caused by the blood flow on a blood vessel inner wall of the subject, a power of the blood flow, a flow volume of the blood flow, and a velocity distribution of the blood flow.

9. The ultrasound imaging device of claim 8, wherein the display unit is further configured to display one or more of numerical values of a maximum value, a minimum value, an average value, an integral value, or a proportion of these values for at least one of the spatial distribution or the temporal distribution.

10. The ultrasound imaging device of claim 8, wherein the display unit is further configured to display a process in which the blood flow detection unit calculates a blood flow velocity of the subject.

11. An ultrasound imaging method for imaging an ultrasound image, comprising:
   irradiating an ultrasound wave to a subject and receiving a reflected signal; and
   detecting a blood flow velocity in the subject using the reflected signal; and
   recognizing a tissue shape of the subject using the reflected signal;
   wherein the detecting the blood flow includes:
      removing an image portion indicating a tissue shape of the subject based on a plurality of ultrasound images of the subject created by using the reflected signal at different times,
      calculating a blood flow velocity vector in the subject based on a plurality of images at different times in which the image portion indicating the tissue shape of the subject is removed,
      identifying a boundary surface between a tissue of the subject and a blood flow based on a recognition result of the shape recognition unit, and
      calculating or correcting the blood flow velocity by applying a consistent condition under a fluid mechanics on the boundary surface.

12. A non-transitory computer-readable medium storing executable instructions that, in response to execution, cause a computer to perform operations comprising:
   irradiating an ultrasound wave to a subject and receiving a reflected signal;
   detecting a blood flow velocity in the subject using the reflected signal; and
   recognizing a tissue shape of the subject using the reflected signal;
   wherein the detecting the blood flow includes:
      removing an image portion indicating a tissue shape of the subject based on a plurality of ultrasound images of the subject created by using the reflected signal at different times, calculating a blood flow velocity vector in the subject based on a plurality of images at different times in which the image portion indicating the tissue shape of the subject is removed, identifying a boundary surface between a tissue of the subject and a blood flow based on a recognition result of the shape recognition unit, and calculating or correcting the blood flow velocity by applying a consistent condition under a fluid mechanics on the boundary surface.

* * * * *